(12) United States Patent
Tuohey

(10) Patent No.: US 11,987,779 B2
(45) Date of Patent: *May 21, 2024

(54) FLEXIBLE BAG

(71) Applicant: GLOBAL LIFE SCIENCES SOLUTIONS USA LLC, Marlborough, MA (US)

(72) Inventor: Colin R. Tuohey, Marlborough, MA (US)

(73) Assignee: GLOBAL LIFE SCIENCES SOLUTIONS USA LLC, Marlborough, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/140,181

(22) Filed: Apr. 27, 2023

(65) Prior Publication Data

US 2023/0265376 A1 Aug. 24, 2023

Related U.S. Application Data

(63) Continuation of application No. 16/757,579, filed as application No. PCT/EP2018/079298 on Oct. 25, 2018, now Pat. No. 11,674,115.

(60) Provisional application No. 62/579,195, filed on Oct. 31, 2017.

(51) Int. Cl.
  *C12M 1/00* (2006.01)
  *C12M 1/06* (2006.01)

(52) U.S. Cl.
  CPC ............ *C12M 23/14* (2013.01); *C12M 27/02* (2013.01); *C12M 29/26* (2013.01)

(58) Field of Classification Search
  CPC ....... C12M 23/14; C12M 27/02; C12M 29/26
  See application file for complete search history.

(56) References Cited

U.S. PATENT DOCUMENTS

| | | | |
|---|---|---|---|
| 5,865,541 A | 2/1999 | Lafleur | |
| 6,127,168 A * | 10/2000 | Ko | C12M 23/14 47/65.5 |
| 2009/0188211 A1 | 7/2009 | Galliher et al. | |
| 2014/0349385 A1 | 11/2014 | Erdenberger et al. | |

FOREIGN PATENT DOCUMENTS

| | | |
|---|---|---|
| CN | 106232478 | 12/2016 |
| DE | 202006014665 | 11/2006 |
| JP | 2014121302 | 7/2014 |
| JP | 2016-010392 A | 1/2016 |

(Continued)

OTHER PUBLICATIONS

Corresponding China Office Action dated Aug. 26, 2023.
(Continued)

*Primary Examiner* — Anshu Bhatia
(74) *Attorney, Agent, or Firm* — Grogan, Tuccillo & Vanderleeden LLP

(57) ABSTRACT

A flexible bioprocess bag comprising a number of flexible panels which are sealed to each other such that when the bag is filled they form at least a bottom of the bag and a side surface of the bag, wherein one of the flexible panels is called a bottom panel and when the bag is filled said bottom panel will constitute the bottom of the bag and parts of the side surface of the bag, said parts of the side surface being bent side parts of the bottom panel.

18 Claims, 7 Drawing Sheets

(56) References Cited

FOREIGN PATENT DOCUMENTS

| | | |
|---|---|---|
| JP | 2016007164 | 1/2016 |
| JP | 2016010392 | 1/2016 |
| WO | 2007112383 | 10/2007 |
| WO | 2014203135 | 12/2014 |
| WO | 2016179236 | 11/2016 |
| WO | 2017064058 | 4/2017 |
| WO | 2019029913 | 2/2019 |

OTHER PUBLICATIONS

Other: English translation of China Office Action.
Bioreactors and Flexsafe STR Bags—A perfect Match for True Scalability in single use 02/201 ?(sartorius stedim).
CFD for Characterizing Standard and Single-use Stirred Cell Culture Bioreactors Jul. 2011 (Stephan C. Kaiser et al.).
Photo 1 in ESACT 2013 (Sartorius)—23rd European Society for Animal Cell Technology (ESACT) Meeting: Better Cells for Better Health Dec. 4, 2013.
Photo 2 in ESACT 2013 (Sartorius)—23rd European Society for Animal Cell Technology (ESACT) Meeting: Better Cells for Better Health Dec. 4, 2013.
23rd European Society for Animal Cell Technology (ESACT) Meeting: Better Cells for Better Health Dec. 4, 2013.
European Search Report dated Aug. 28, 2023 for corresponding European Application No. 18 796 396.2.

\* cited by examiner

FLEXIBLE BAG

CROSS-REFERENCE TO RELATED APPLICATION

The present patent application is a continuation of U.S. patent application Ser. No. 16/757,579, filed Apr. 20, 2020, which is a National Stage application, filed under 35 U.S.C. § 371, of the International Patent Application No. PCT/EP2018/079298 filed on Oct. 25, 2018, which claims priority to U.S. Provisional Patent Application No. 62/579,195, filed Oct. 31, 2017, all of which are hereby incorporated by reference in their entireties.

TECHNICAL FIELD OF THE INVENTION

The present invention relates to a flexible bioprocess bag comprising a number of flexible panels. In particular, it relates to large scale flexible bioprocess bags for use as single use liners in cylindrical bioreactor or mixer vessels. It also relates to a cylindrical bioreactor or mixer, a method of loading a flexible bioprocess bag in a cylindrical bioreactor or mixer and a method of cultivating cells in a cylindrical bioreactor vessel.

RELATED ART

Flexible bags for holding and possibly handling fluids can be provided in different ways. Flexible panels may be sealed to each other to make up a bag of a suitable form. In for example a bioreactor a cylindrical vessel is often used and a flexible bag is provided inside the vessel as a disposable liner. If a liner which is not matching the form of the vessel in a good way is provided into the vessel there may be wrinkles in the liner or areas of stress concentration from the fluid head pressure pushing on the film in an unsupported region. Wrinkles may cause problems with fluid getting stacked in the wrinkles. Furthermore, in for example bioreactors a close fit between the form of the vessel and the liner is suitable for improving heat transfer.

SUMMARY

An object of the invention is to provide an improved flexible bioprocess bag.

A further object of the invention is to provide a flexible bag fitting close inside a cylindrical vessel that minimizes film folds.

This is achieved in a flexible bag according to claim 1.

According to one aspect of the invention a flexible bioprocess bag is provided comprising a number of flexible panels which are sealed to each other such that when the bag is filled they form at least a bottom of the bag and a side surface of the bag, wherein one of the flexible panels is called a bottom panel and when the bag is filled said bottom panel will constitute the bottom of the bag and parts of the side surface of the bag, said parts of the side surface being bent side parts of the bottom panel.

Hereby a flexible bioprocess bag is achieved with an improved design which provides a robust bag with suitable geometry. The flexible bag according to the invention is suitable for use inside a cylindrical vessel. Wrinkles and film folds are minimized when the flexible bag is provided inside a cylindrical vessel and hereby stagnant fluid zones can be eliminated or decreased. In such stagnant fluid zones suspended solids can accumulate in for example a mixing bag or a bioreactor. This can thus be avoided by the present invention. Furthermore, with the flexible bag according to the invention it can be ensured that the film layer is kept thin between the process fluid and a vessel surface without pockets of entrapped air that can form from film folds. This is suitable for improving heat transfer. Furthermore, with a flexible bag according to the invention fluid hold up in the bag during draining can be reduced.

According to another aspect of the invention a cylindrical bioreactor or mixer comprising the flexible bioprocess bag according to the invention is provided.

According to another aspect of the invention a method of loading a flexible bioprocess bag in a cylindrical bioreactor or mixer is provided. The method comprises the steps of:
  providing a cylindrical bioreactor or mixer vessel;
  providing the flexible bioprocess bag as described above;
  loading said flexible bioprocess bag in said cylindrical bioreactor or mixer vessel.

According to another aspect of the invention a method of cultivating cells in a cylindrical bioreactor vessel is provided. Said method comprises the steps of:
  loading a flexible bioprocess bag in a cylindrical bioreactor vessel according to the method as described above;
  providing a cell culture medium to an inner volume of said flexible bioprocess bag;
  providing cells to the inner volume of said flexible bioprocess bag;
  cultivating the cells in the inner volume under agitation.

In one embodiment of the invention said bent side parts of the bottom panel are two essentially triangular parts of the side surface of the bag.

In one embodiment of the invention the bottom panel is an elongated panel comprising a middle part having two opposite first side edges, said elongated panel further comprising two essentially triangular parts connected one to each of the first side edges of the middle part. The two essentially triangular parts may each have a base integral with the middle part and two edges converging towards a top.

In one embodiment of the invention said middle part is essentially a quadrilateral with side edges of substantially the same length as a diameter of a cylinder substantially matching the form of the side surface of the bag when the bag is filled, wherein said essentially triangular parts are connected along its bases one to each of said first side edges of the middle part with the tops of the triangular parts pointing away from each other.

In one embodiment of the invention the two first side edges of the middle part where the bases of the essentially triangular parts are connected are shorter than two remaining side edges, called second side edges of the middle part and the two second side edges are curved such that a circle having the same diameter as a cylinder substantially matching the form of the side surface of the bag when the bag is filled still fits inside the middle part.

In one embodiment of the invention an angle of a top of the essentially triangular parts is within the range of 75-105 degrees. In one embodiment of the invention an angle of a top of the essentially triangular parts is within the range of 85-95 degrees.

In one embodiment of the invention the flexible panels of the bag comprise the bottom panel and furthermore two side panels each comprising two side edges which side panels are sealed to each other along its side edges and sealed to the bottom panel to form an essentially cylindrical side surface together with the essentially triangular parts of the bottom panel.

In one embodiment of the invention the flexible panels of the bag comprise the bottom panel and furthermore one single side panel having two side edges which are sealed to each other and said single side panel is also sealed to the bottom panel to form an essentially cylindrical side surface together with the essentially triangular parts of the bottom panel.

In one embodiment of the invention the flexible panels of the bag further comprise a top panel essentially of the same form as the bottom panel and one or more side panels, said flexible panels being sealed to each other such that a closed bag of essentially cylindrical form is achieved when the bag is filled.

In one embodiment of the invention at least one connector is provided to any one of the flexible panels for the purpose of exchanging fluid from an external space to an internal space of the bag.

In one embodiment of the invention at least one impeller is provided to any one of the flexible panels for the purpose of mixing content inside the bag.

In one embodiment of the invention at least one sensor is provided to any one of the flexible panels for the purpose of measuring one or more physical or chemical attributes of the content in the bag.

In one embodiment of the invention said flexible bag is a liner for a cylindrical bioreactor vessel or mixer.

BRIEF DESCRIPTION OF THE DRAWINGS

FIG. 1b is a schematic side view of the same filled flexible bag as shown in FIG. 1a.

DETAILED DESCRIPTION OF EMBODIMENTS

A flexible bag is provided comprising a number of flexible panels which are sealed to each other such that when the bag is filled they form at least a bottom of the bag and a side surface of the bag. According to the invention one of the flexible panels is called a bottom panel and when the bag is filled said bottom panel will constitute the bottom of the bag and parts of the side surface of the bag. Said parts of the side surface of the bag being bent side parts of the bottom panel. In some embodiments of the invention said bent side parts of the bottom panel are two essentially triangular parts. Essentially triangular would in this patent application include a triangle but also include a triangle having somewhat curved sides instead of straight sides, i.e. an essentially triangular part comprises one base and two sides converging to meet each other, where both the base and the sides can be somewhat curved or straight. The bent side parts can in another embodiment of the invention be quadrilateral instead of triangular.

Figure 1A:
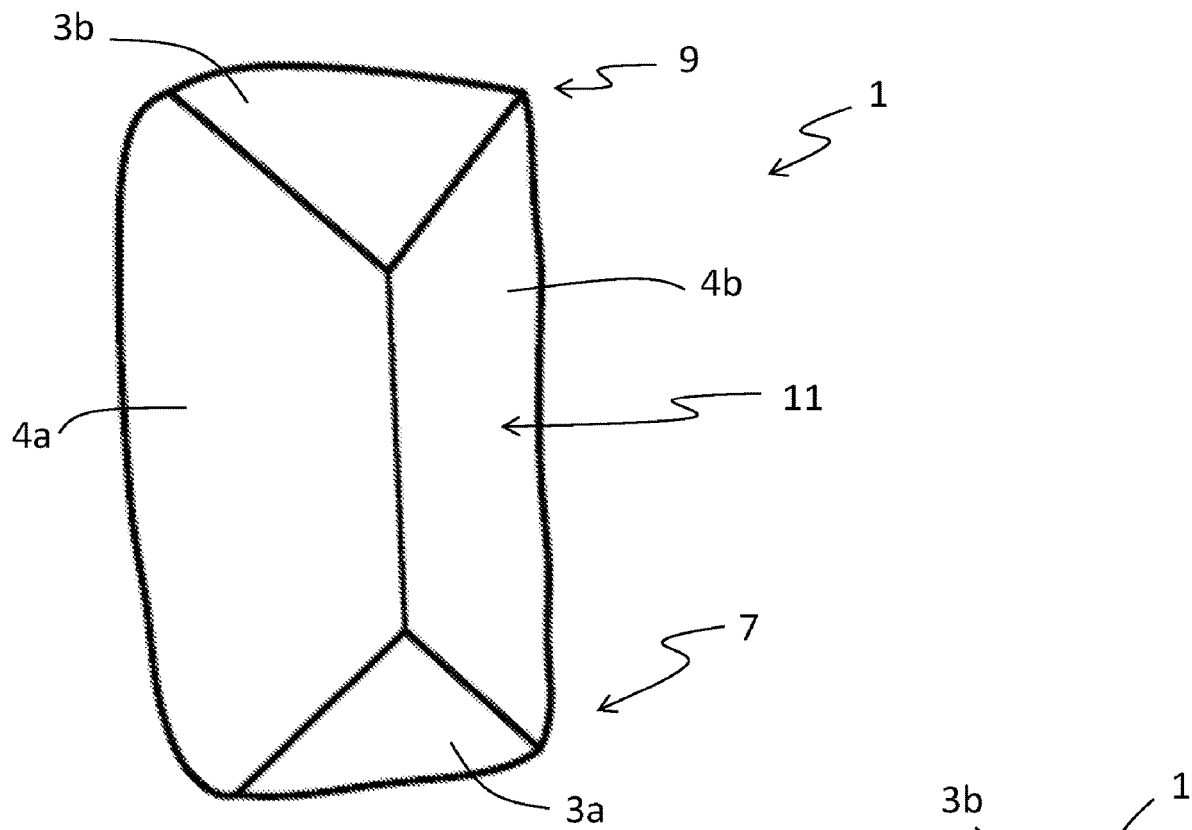
FIG. 1a is a schematic front view of a filled flexible bag according to one embodiment of the invention.
Figure 1B:
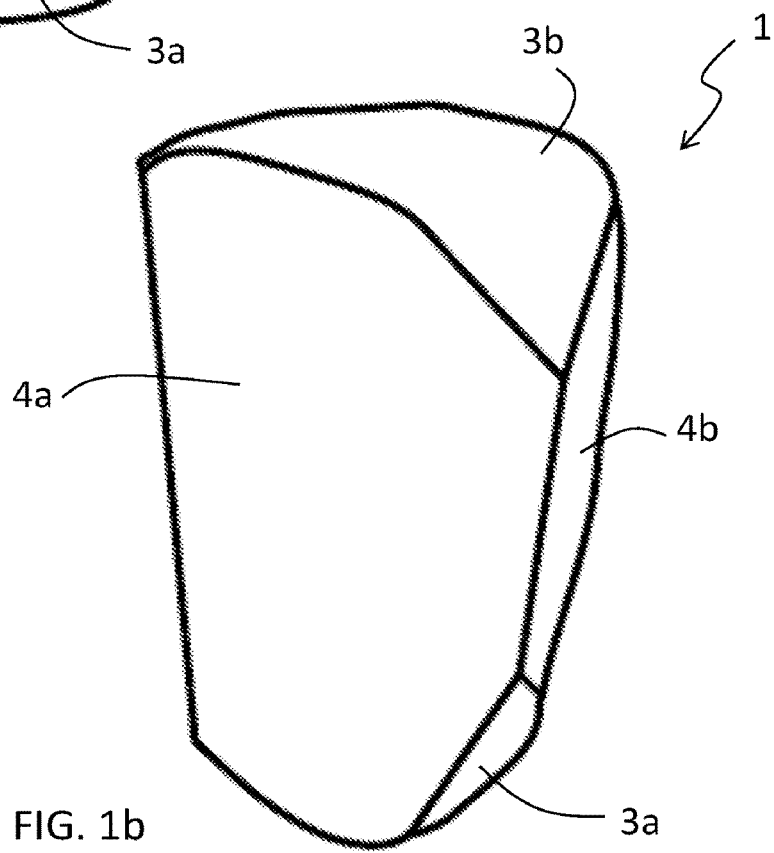
Figure 1C:
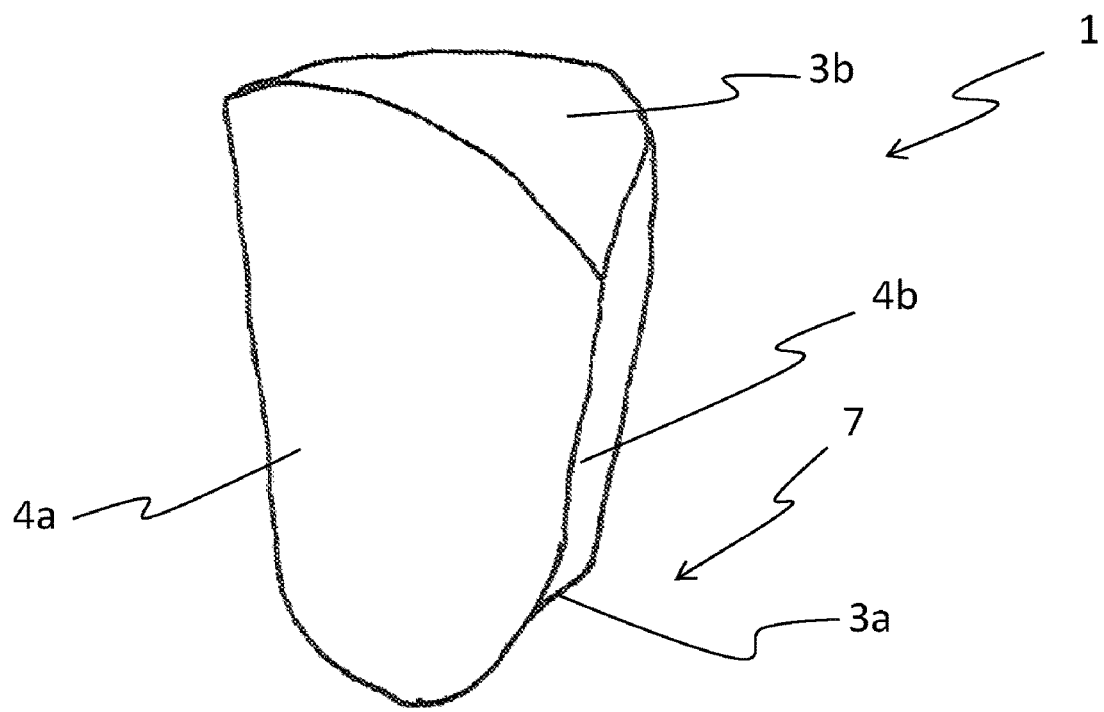
FIG. 1c is a schematic perspective view of the flexible bag as shown in FIGS. 1a and 1b.
Figure 1D:
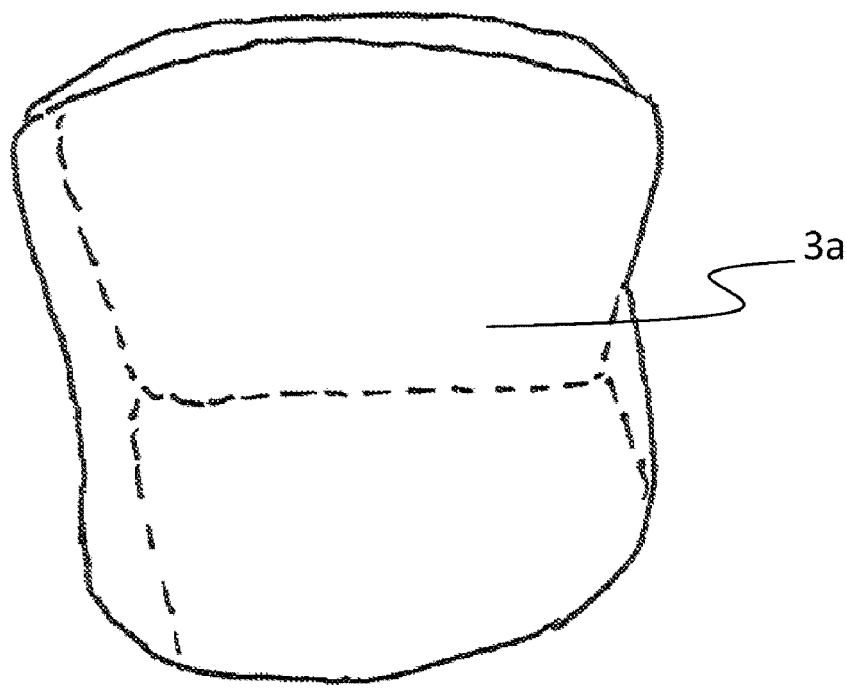
FIG. 1d is a schematic perspective view from the bottom of the flexible bag as shown in FIGS. 1a, b and c.

FIG. 1a is a schematic front view of a filled flexible bag 1 according to one embodiment of the invention and FIG. 1b is a schematic side view of the same filled flexible bag as shown in FIG. 1a. FIG. 1c is a schematic perspective view of the same flexible bag as shown in FIGS. 1a and 1b. FIG. 1d is a schematic perspective view from the bottom of the same flexible bag as shown in FIGS. 1a, b and c.

The flexible bag 1 according to this embodiment of the invention comprises four flexible panels 3a, 3b, 4a, 4b which are sealed to each other such that when the bag is filled they form a bottom 7 of the bag, a top 9 of the bag and a side surface 11 of the bag. One of the flexible panels is called a bottom panel 3a and when the bag is filled said bottom panel 3a will constitute both the bottom 7 of the bag and parts of the side surface 11. Said parts of the side surface 11 are bent side parts 10a, 10b of the bottom panel 3a. Two bent side parts 10a, 10b of the bottom panel 3a are in this embodiment essentially triangular and are also called essentially triangular parts 10a, 10b. These bent side parts, also called triangular parts 10a, 10b can be better seen in FIG. 2. The bent side parts 10a, 10b will be bent from the bottom 7 to form parts of the side surface 11. In this embodiment the bent side parts 10a, 10b are essentially triangular in form however in other embodiments of the invention the bent side parts 10a, 10b can have other geometries, such as quadrilateral. In the embodiment of the invention as shown in FIGS. 1a-1d there is also a top panel 3b having the same geometry and dimensions as the bottom panel 3a. In another embodiment of the invention a top 9 of the bag can be designed differently. For example, the side panels 4a, 4b can be sealed together to provide a closure at the top of the bag. Geometry of a bottom panel 3a and possibly also a top panel 3b according to some embodiments of the invention is discussed in further detail in relation to FIG. 2. FIG. 3a shows one example of a bottom panel 3a which can be used in a flexible bag according to one embodiment of the invention and FIG. 3b shows one example of a top panel 3b which can be used in a flexible bag according to one embodiment of the invention.

Figure 4A:
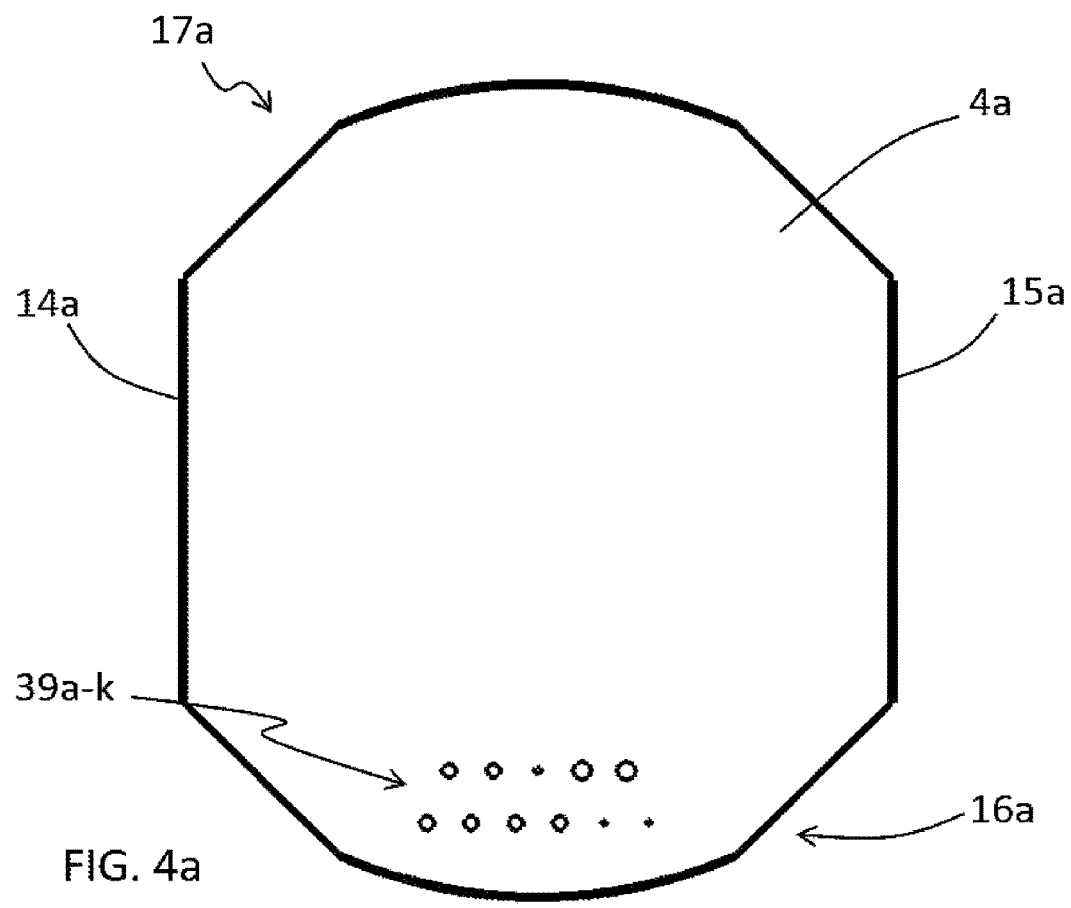
FIG. 4a is a schematic view of a first side panel of a flexible bag according to one embodiment of the invention.
Figure 4B:
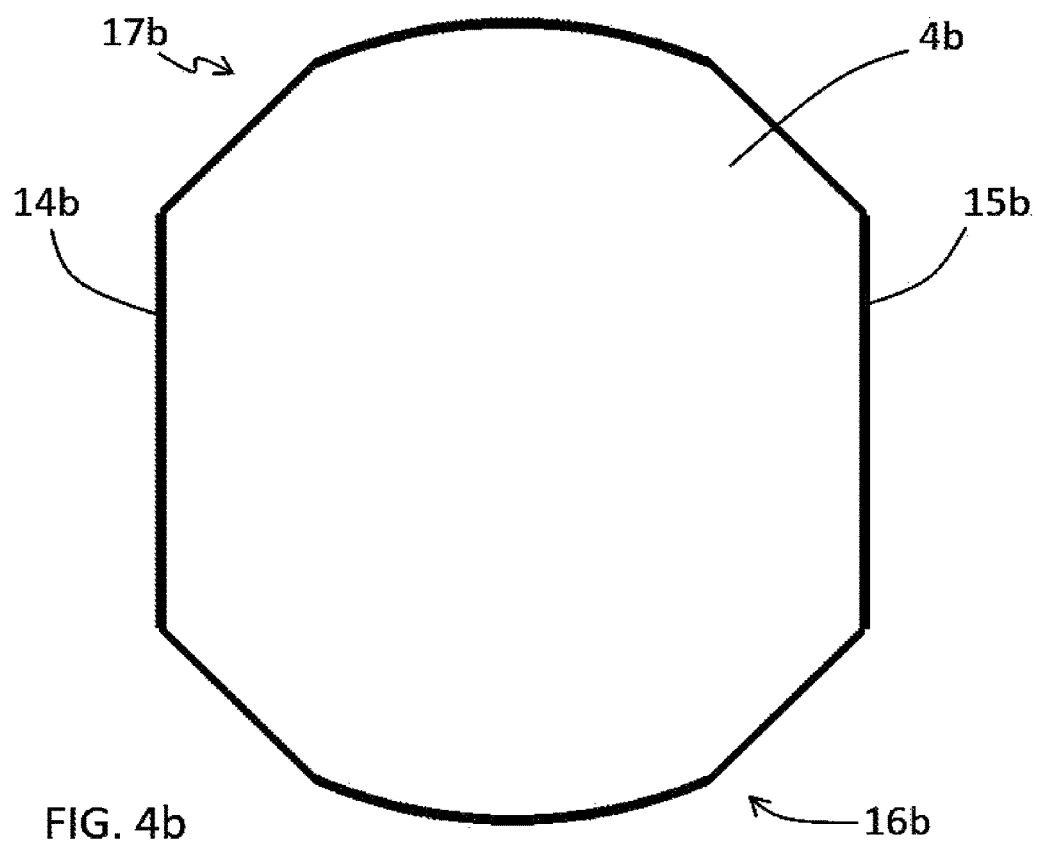
FIG. 4b is a schematic view of a second side panel of a flexible bag according to one embodiment of the invention.

The flexible bag 1 according to this embodiment comprises further two side panels 4a, 4b. Said two side panels 4a, 4b are identical in form and dimensions and comprises each two side edges 14a, 15a, 14b, 15b, see FIGS. 4a and 4b. Each side edge of said side panels is sealed to one of the side edges of the other side panel such that an enclosing side surface 11 of the bag is achieved. Furthermore, the side panels 4a, 4b are sealed to the bottom panel 3a to form an essentially cylindrical side surface 11 together with the essentially triangular parts 10a, 10b of the bottom panel 3a. In FIGS. 4a and 4b two examples of side panels 4a, 4b according to one embodiment of the invention is shown. In another embodiment of the invention only one single side panel 4 is provided, see FIG. 6. In that embodiment of the invention the single side panel 4 is wrapped around the circumference of the bag and the side edges of the single side panel 4 are sealed to each other. The single side panel 4 is furthermore sealed to the bottom panel such that an essentially cylindrical side surface is formed together with the essentially triangular parts 10a, 10b of the bottom panel 3a. In still another embodiment of the invention more than two side panels are provided. Any number of side panels could be provided. Said side panels are sealed to make up an overall geometry essentially as the one shown in FIG. 6.

The flexible bag 1 of FIGS. 1*a*-1*d* can be folded when empty. This is suitable for transport and/or storage. The design of the flexible panels allows it to be folded flat when empty. The convergence of the side panels and the top or bottom panels into a triangular point provides a natural fold line in three locations (horizontally alongside panel 4*a* or 4*b* from triangular point to point and along the horizontal central axis of top or bottom panel 3*a* or 3*b*), so that the top and bottom panel can be folded flat either over or under the side surface. This is especially advantageous when rigid ports and tubing are attached to the film panel restricting its ability to easily fold in certain directions. All seams can be joined together through the process of heat sealing in a reliable and easy manner when the bag of this panel construction is compressed in the flat state enabling robust manufacturing of the bag.

Figure 2:
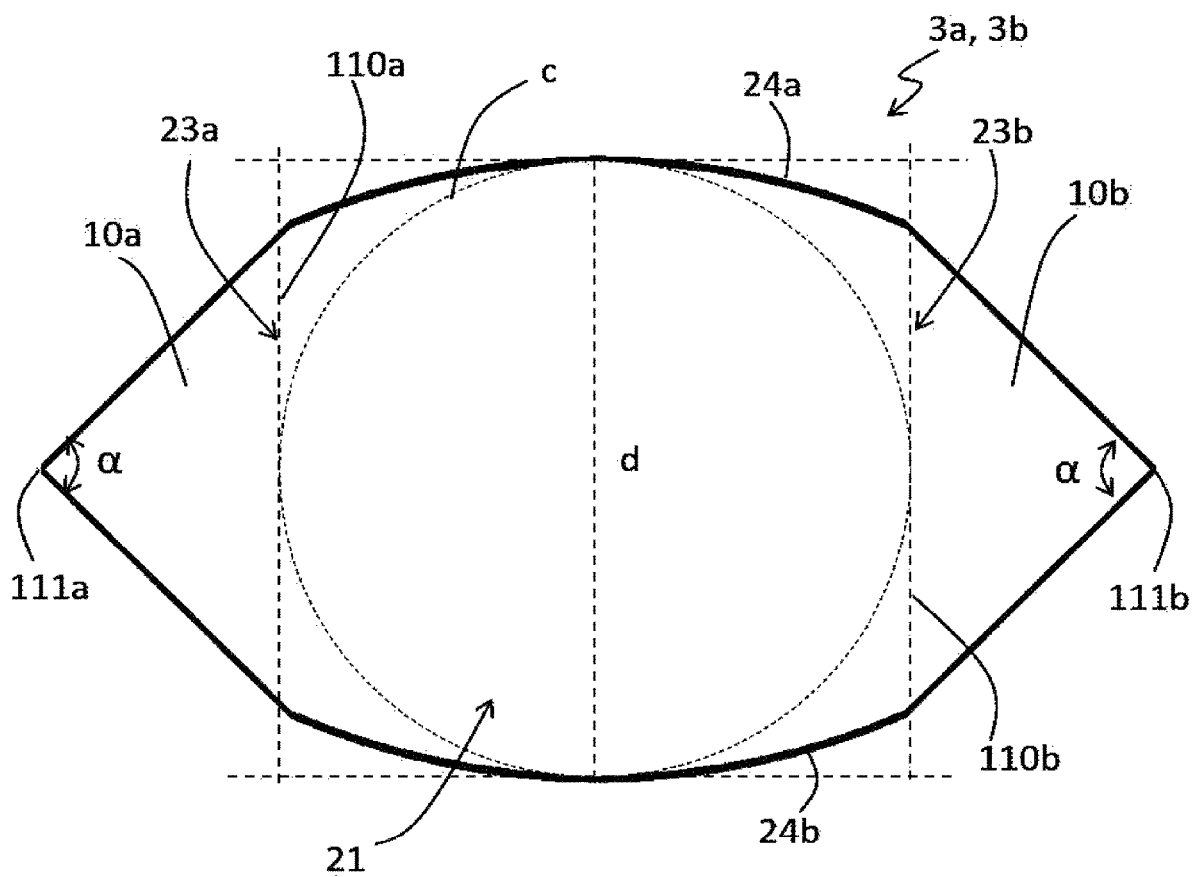
FIG. 2 shows schematically a bottom panel of a flexible bag according to one embodiment of the invention.
Figure 3A:
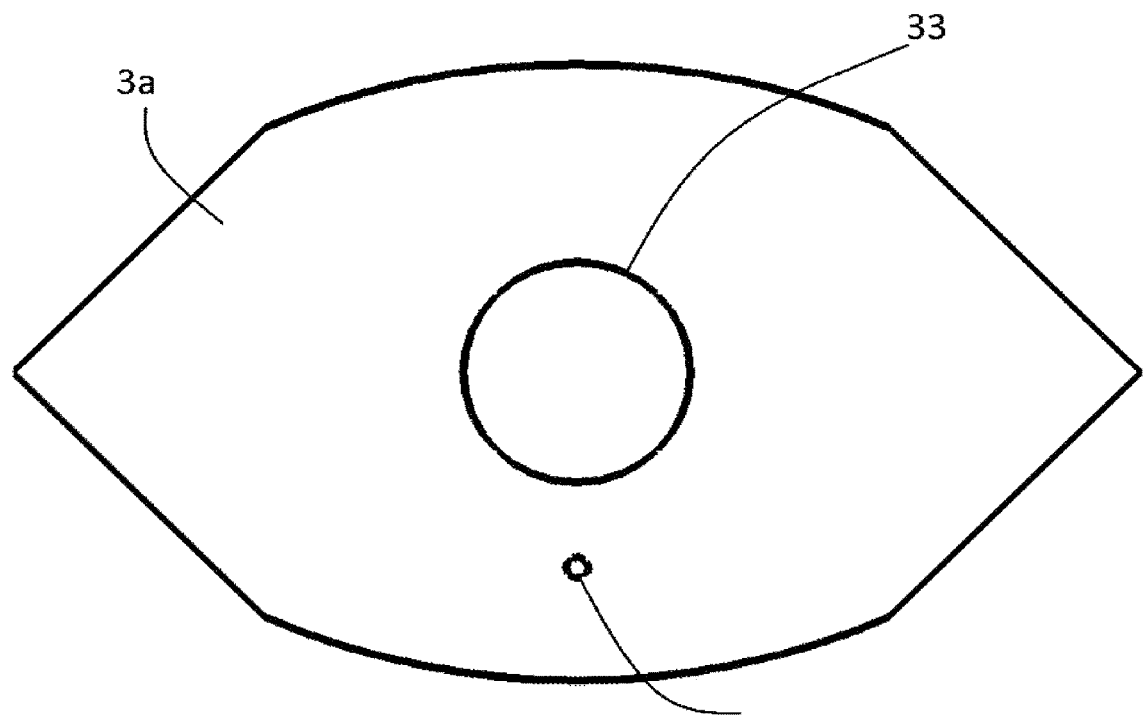
FIG. 3a is a schematic view of a bottom panel of a flexible bag according to one embodiment of the invention.
Figure 3B:
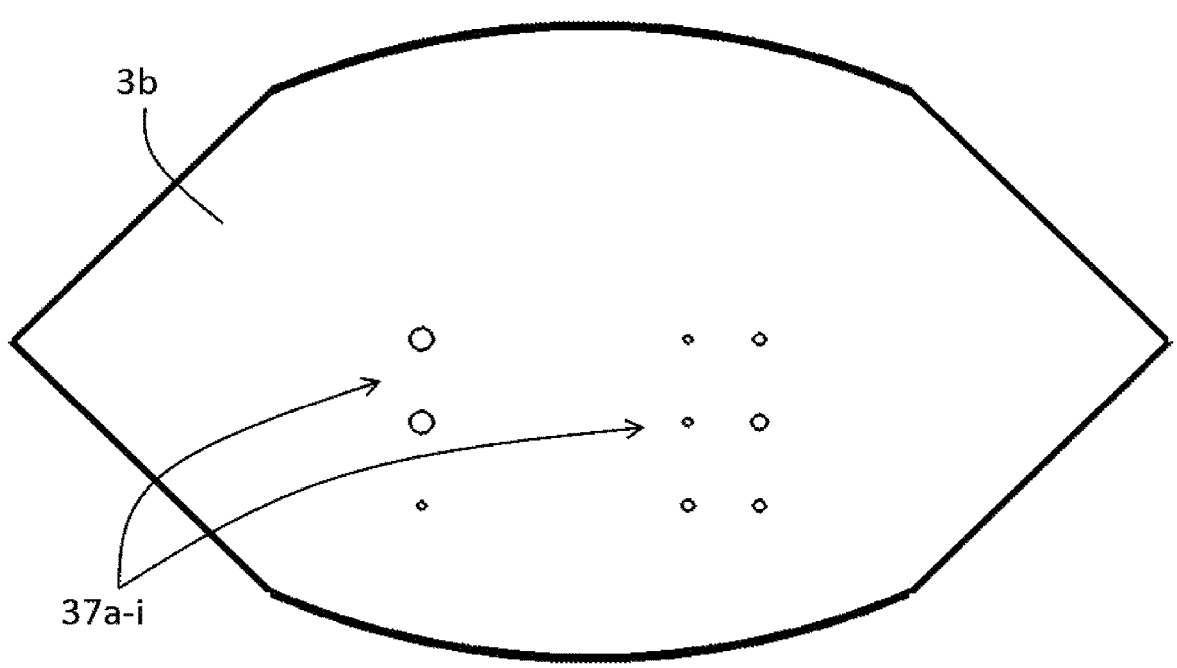
FIG. 3b is a schematic view of a top panel of a flexible bag according to one embodiment of the invention.

FIG. 2 shows schematically the design of a bottom panel 3*a* according to one embodiment of the invention. As discussed above the design of a top panel 3*b* can be identical however in the text describing FIG. 2 it is referred to a bottom panel 3*a*. The bottom panel 3*a* is an elongated panel comprising a middle part 21 and two essentially triangular parts 10*a*, 10*b*. The middle part 21 comprises two opposite first side edges 23*a*, 23*b* and the triangular parts 10*a*, 10*b* are connected one to each of said first side edges 23*a*, 23*b* of the middle part 21. Said middle part 21 is essentially a quadrilateral with four side edges. Two of the side edges are the two first side edges 23*a*, 23*b* mentioned above and the two remaining side edges are called second side edges 24*a*, 24*b* and are also positioned opposite each other. The first and second side edges 23*a*, 23*b*, 24*a*, 24*b* are all of substantially the same length as a diameter d of a cylinder substantially matching the form of the side surface 11 of the bag when the bag is filled. Said essentially triangular parts 10*a*, 10*b* are connected along its bases 110*a*, 110*b* one to each of the two first side edges 23*a*, 23*b* of the middle part with a top 111*a*, 111*b* of the triangular parts 10*a*, 10*b* pointing away from each other.

In this embodiment of the invention the two first side edges 23*a*, 23*b* of the middle part 21 where the bases 110*a*, 110*b* of the essentially triangular parts 10*a*, 10*b* are connected are shorter than the two second side edges 24*a*, 24*b* of the middle part 21 and the two second side edges 24*a*, 24*b* are curved such that a circle c having the same diameter d as a cylinder substantially matching the form of the side surface 11 of the bag 1 when the bag is filled still fits inside the middle part 21. Since the cylinder of diameter d fits inside the middle part 21, the triangular parts 10*a* and 10*b* when extending up in the inflated portion do not have to support the force exerted by the fluid head pressure while unsupported by the tank. This prevents excessive stress at the tri-seam area by having the triangular parts 10*a* and 10*b* always in contact with the vessel surface. Any gaps between the film and the vessel, especially in this location, can cause the fluid head pressure to exert a force against the triangular part which pulls down one panel of the tri-seam and can cause leaks. In this way, the panel geometry optimizes the amount of surface to surface contact between the film and the vessel support structure without the use of excess film that can lead to wrinkles.

The angle α of the tops 111*a*, 111*b* of the two essentially triangular parts 10*a*, 10*b* is within the range of 75-105 degrees. In one embodiment of the invention the angle α is within the range of 85-95 degrees and in one embodiment of the invention the angle α is 90 degrees.

This design of a bottom panel 3*a* of the flexible bag 1 according to the invention will provide a flexible bag which can be provided as a liner inside a cylindrical vessel, for example a bioreactor, with some important advantages. One advantage with this design of a flexible bag is that wrinkles can be avoided in the part of the flexible bag where the bottom 7 of the bag meets the side surface 11 of the bag. The triangular parts 10*a*, 10*b* of the bottom panel 3*a* which will be folded up from the bottom to constitute parts of the side surface 11 of the bag contributes to decreased risk of wrinkles. The design can also accommodate protrusions such as baffles (used to enhance bioreactor mixing performance) which increases the circumference of the tank for a fixed tank diameter. The circumference of the bag is increased by increasing the panel width while decreasing extra film that would result in wrinkles through the curvature formed by the arcs 24*a* and 24*b* (curved form of second side edges 24*a*, 24*b*) in FIG. 2. Furthermore, the angle of the tops of the triangular parts 10*a*, 10*b* being in one embodiment essentially 90 degrees or within the range of 75-105 degrees will facilitate a vertical orientation of the bag when it is filled since the straight side panel seams when joined together will not cause the top or bottom panel to buckle when inserted into a cylinder with a vertical side wall at 90 degrees to its bottom surface.

In some embodiments of the invention one or more connectors can be provided to any one of the flexible panels 3*a*, 3*b*, 4*a*, 4*b* for the purpose of exchanging fluid from an external space to an internal space of the bag 1. Furthermore, one or more impellers can be provided to any one of the flexible panels 3*a*, 3*b*, 4*a*, 4*b* for the purpose of mixing content inside the bag 1. Furthermore, one or more sensors can be provided to any one of the flexible panels 3*a*, 3*b*, 4*a*, 4*b* for the purpose of measuring one or more physical or chemical attribute of the content in the bag 1.

FIGS. 3*a*, 3*b*, 4*a* and 4*b* show schematically the flexible panels of a flexible bag according to one embodiment of the invention. FIG. 3*a* shows a bottom panel 3*a*, FIG. 3*b* shows a top panel 3*b*, FIG. 4*a* shows a first side panel 4*a* and FIG. 4*b* shows a second side panel 4*b*. In this embodiment of the invention the bottom panel 3*a* comprises an impeller 33 and a connector and/or sensor 35. The top panel 3*b* comprises 9 different connectors and/or sensors 37*a-i* and the first side panel 4*a* comprises 11 different connectors and/or sensors 39*a-k*. The number of connectors/sensors can of course be varied. Connector/sensors can as well be provided to the second side panel 4*b*.

The first and second side panels 4*a*, 4*b* comprises as described above each two opposite side edges 14*a*, 15*a*, 14*b*, 15*b* which each is sealed to one side edge of the other side panel to form an enclosing side surface 11 of the flexible bag 1. The two remaining edges of each of the side panels 4*a*, 4*b* are called bottom panel sealing edge 16*a*, 16*b* and top panel sealing edge 17*a*, 17*b*. The bottom panel sealing edges 16*a*, 16*b* and the top panel sealing edges 17*a*, 17*b* are formed to match the design of the bottom panel 3*a* and the top panel 3*b* when the triangular parts 10*a*, 10*b* are folded up constituting parts of the side surface 11 of the flexible bag 1.

Figure 5:
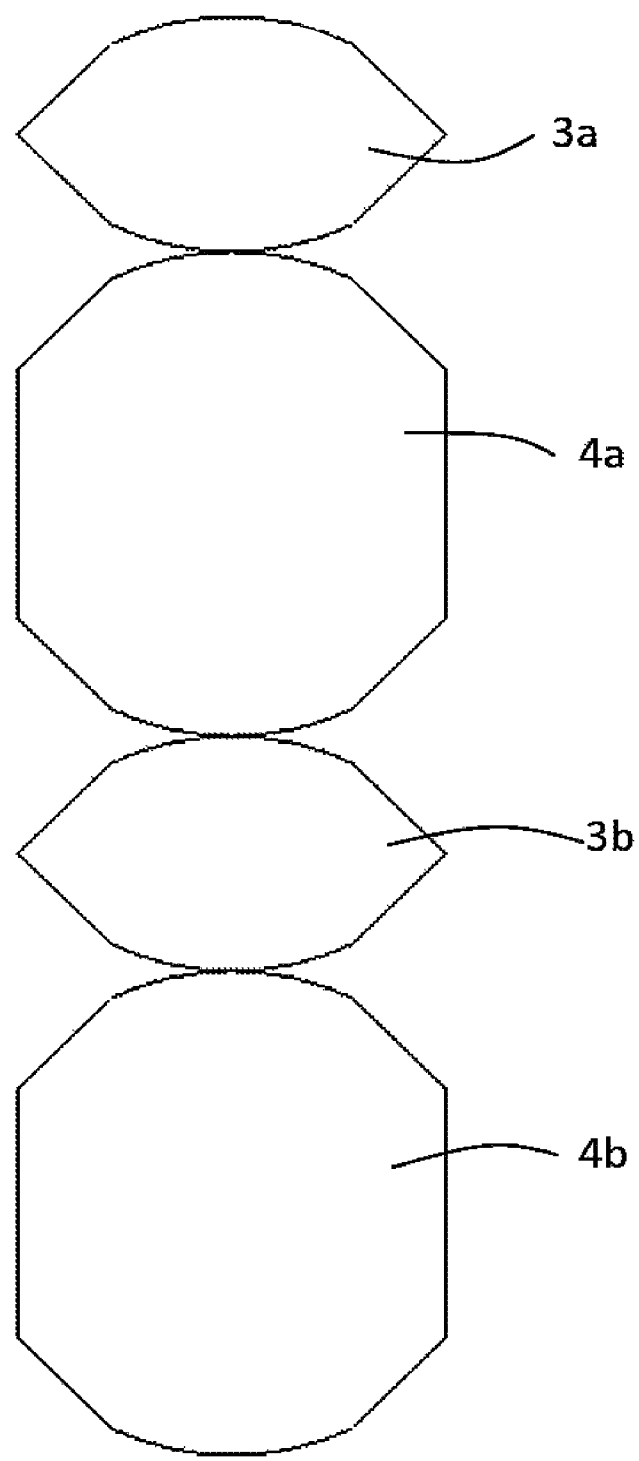
FIG. 5 is a schematic view of flexible panels of a flexible bag before sealing of the panels to form a bag according to one embodiment of the invention.

FIG. 5 shows one embodiment of the invention where the flexible panels 3*a*, 3*b*, 4*a*, 4*b* are cut out from one single piece of flexible sheet and in this embodiment, the number of seals required to form the three-dimensional bag is reduced because the panels are joined at the adjacent tangent edges of the joining arc segments. Misalignment during fabrication of the panels is reduced because there is just one sheet of film that is folded and sealed at the edges.

Figure 6:
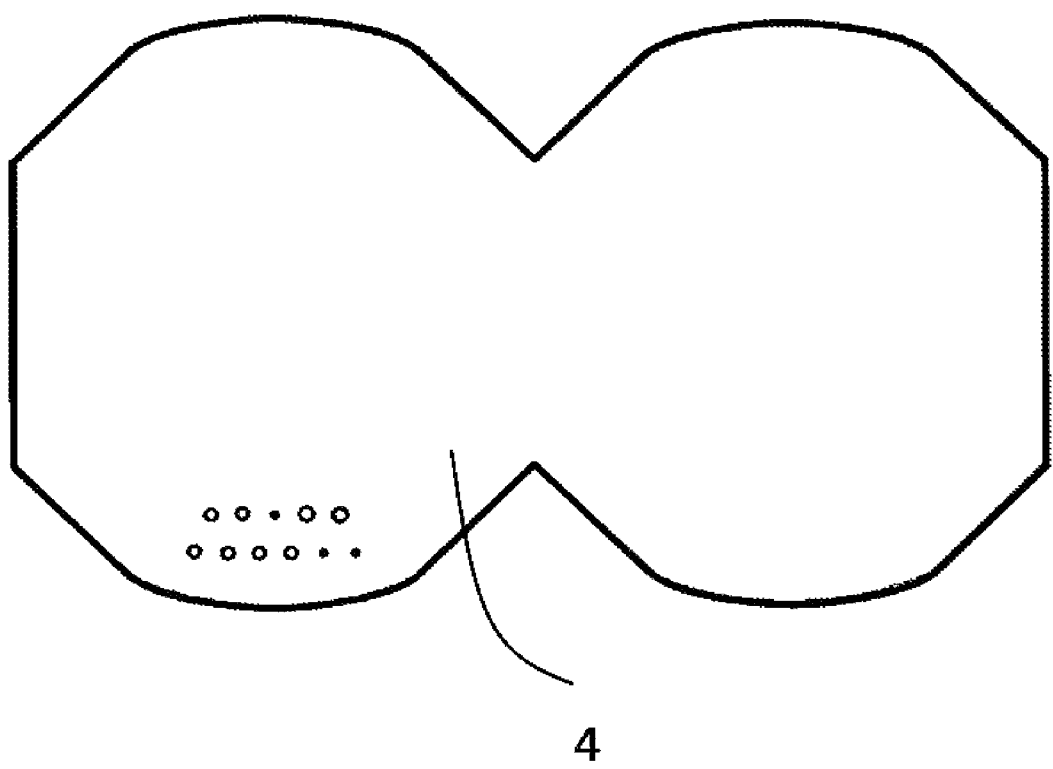
FIG. 6 is a schematic view of a single side panel of a flexible bag according to another embodiment of the invention.

FIG. 6 is a schematic view of a single side panel 4 of a flexible bag according to another embodiment of the invention. In this embodiment of the invention one single side panel 4 is provided instead of two side panels 4a, 4b as shown in FIGS. 4a and 4b.

In one embodiment of the invention the internal volume of the flexible bag when filled is at least 10 L, such as at least 50 L. The internal volume can be up to 1 m3 or even 2 m3, with the advantages of reduced fold/wrinkle formation and reduced stress concentration being particularly pronounced for larger bags, e.g. in the 50 L to 2 m3 interval. In one embodiment of the invention the flexible bag is presterilized, e.g. by gamma irradiation.

The flexible bag according to the invention can be provided as a liner for a cylindrical vessel, for example a bioreactor vessel. The dimensions of such a liner should be adapted to the dimensions of the vessel and specifically the circumference of the essentially cylindrical side surface of the bag should closely match the circumference of the vessel including any number of protruding internal surfaces in the vessel, for example baffles. In one example, baffles can take the shape of a triangular protrusion with one side joined at the vessel side wall and extending into the inner region of the vessel between $1/10$ and $1/12$ of the tank diameter. These baffles are commonly used to improve the mixing performance in cylindrical tanks.

It may be important to provide a liner (flexible bag) which will stay as close as possible to an inner wall of a vessel. This can be important for heat transferring and for supporting of the flexible bag and avoidance of tension to the seals of the flexible bag. Furthermore, as described above wrinkles in the flexible bag should be avoided. The flexible bag according to the invention is suitable regarding all these aspects. An essentially cylindrical flexible bag is provided according to the invention which can stay close to the inner walls of a cylindrical vessel and which reduces risk of wrinkles especially where a bottom of the flexible bag turns into a side surface.

A cylindrical bioreactor or mixer comprising the flexible bioprocess bag according to the invention is also provided. Such a cylindrical bioreactor or mixer can have a flat bottom or a bottom being somewhat elliptical or conical. The bottom may e.g. have a frustoconical or spherical cap shape, optionally with one or more openings for attachment of an impeller drive, drainage tubing and/or supply lines for gases or liquids.

Furthermore, a method of loading a flexible bioprocess bag in a cylindrical bioreactor or mixer is provided. The method comprises the steps of:
providing a cylindrical bioreactor or mixer vessel;
providing the flexible bioprocess bag as described above;
loading said flexible bioprocess bag in said cylindrical bioreactor or mixer vessel.

Furthermore, a method of cultivating cells in a cylindrical bioreactor vessel is provided. Said method comprises the steps of:
loading a flexible bioprocess bag in a cylindrical bioreactor vessel according to the method as described above;
providing a cell culture medium to an inner volume of said flexible bioprocess bag;
providing cells to the inner volume of said flexible bioprocess bag;
cultivating the cells in the inner volume under agitation.

The invention claimed is:

1. A flexible bioprocess bag comprising:
a number of flexible panels which are sealed to each other;
wherein one of the number of flexible panels is a bottom panel, comprising a quadrilateral middle part having two opposite first side edges substantially the same length as a diameter of a cylinder substantially matching a form of a side surface of the bag when the flexible bioprocess bag is filled and placed within a cylindrical bioreactor vessel, said bottom panel further comprising two triangular parts, each connected along their bases to one of the first side edges of the middle part,
wherein the two first side edges of the middle part where the bases of the triangular parts are connected are shorter than two remaining side edges, called second side edges of the middle part,
wherein the two second side edges are curved such that a circle having the same diameter as a cylinder substantially matching the form of the side surface of the bag when the bag is filled and placed within the cylindrical bioreactor vessel still fits inside the middle part, and
when the flexible bioprocess bag is filled said bottom panel will constitute the bottom of the bag and parts of the side surface of the bag, said parts of the side surface being bent side parts of the bottom panel.

2. The flexible bioprocess bag according to claim 1, wherein said bent side parts of the bottom panel are two essentially triangular parts.

3. The flexible bioprocess bag according to claim 2, wherein the tops of the triangular parts point away from each other.

4. The flexible bioprocess bag according to claim 2, wherein an angle of the tops of the triangular parts is within the range of 75-105 degrees.

5. The flexible bioprocess bag according to claim 2, wherein an angle of the tops of the triangular parts is within the range of 85-95 degrees.

6. The flexible bioprocess bag according to claim 1, wherein the number of flexible panels further comprises two side panels sealed to each other along side edges, and
wherein two side panels are sealed to the bottom panel to form an cylindrical side surface together with the bent side parts of the bottom panel when the bag is filled.

7. The flexible bioprocess bag according to claim 1, wherein the number of flexible panels further comprises one single side panel having two side edges which are sealed to each other, and
wherein said single side panel is also sealed to the bottom panel to form a cylindrical side surface together with the bent side parts of the bottom panel.

8. The flexible bioprocess bag according to claim 1, wherein the number of flexible panels further comprises a top panel, said number of flexible panels being sealed to each other such that a closed bag of essentially cylindrical form is achieved when the flexible bioprocess bag is filled and placed within the cylindrical bioreactor vessel.

9. The flexible bioprocess bag according to claim 1, wherein at least one connector is provided to any one of the number of flexible panels for the purpose of exchanging fluid from an external space to an internal space of the flexible bioprocess bag.

10. The flexible bioprocess bag according to claim 1, wherein at least one impeller is provided to any one of the number of flexible panels.

11. The flexible bioprocess bag according to claim 10, wherein the impeller is provided to the bottom panel.

12. The flexible bioprocess bag according to claim 1, wherein at least one sensor is provided to any one of the number of flexible panels.

13. The flexible bioprocess bag according to claim 1, wherein the flexible bioprocess bag has an internal volume when filled of at least 10 L.

14. The flexible bioprocess bag according to claim 1, wherein the flexible bioprocess bag is presterilized.

15. The flexible bioprocess bag according to claim 1, wherein said flexible bioprocess bag is a liner for the cylindrical bioreactor vessel or a mixer.

16. A cylindrical bioreactor or mixer comprising the flexible bioprocess bag of claim 1.

17. A method of loading a flexible bioprocess bag in a cylindrical bioreactor or mixer, comprising the steps of:
   providing a cylindrical bioreactor or mixer vessel;
   providing the flexible bioprocess bag of claim 1;
   loading said flexible bioprocess bag in said cylindrical bioreactor or mixer vessel.

18. A method of cultivating cells in a cylindrical bioreactor vessel, comprising the steps of:
   loading a flexible bioprocess bag in a cylindrical bioreactor vessel according to the method of claim 17;
   providing a cell culture medium to an inner volume of said flexible bioprocess bag;
   providing cells to the inner volume of said flexible bioprocess bag;
   cultivating the cells in the inner volume under agitation.

* * * * *